US005520890A

United States Patent [19]
Lorentzen et al.

[11] Patent Number: 5,520,890
[45] Date of Patent: May 28, 1996

[54] SOLID/LIQUID SLURRY TREATMENT APPARATUS AND CATALYTIC MULTI-PHASE REACTOR

[75] Inventors: Geir B. Lorentzen, Sandnes; Arild Westvik; Trond Myrstad, both of Trondheim, all of Norway

[73] Assignee: Den norske stats oljeselskap A.S, Stavanger, Norway

[21] Appl. No.: 292,733

[22] Filed: Aug. 18, 1994

[30]  Foreign Application Priority Data

Aug. 24, 1993 [GB] United Kingdom ............... 9317605

[51] Int. Cl.$^6$ ................... B01J 8/06; C10J 3/00
[52] U.S. Cl. .............. 422/197; 422/196; 422/198; 422/239
[58] Field of Search .................. 518/700; 422/196, 422/197, 198, 201, 239

[56] References Cited

U.S. PATENT DOCUMENTS

| | | | |
|---|---|---|---|
| 4,102,778 | 7/1978 | Ruether | 208/143 |
| 4,374,095 | 2/1983 | Legg et al. | 422/218 |
| 4,411,869 | 10/1983 | Kroushl et al. | 422/188 |
| 4,464,255 | 8/1984 | Ueda | 210/136 |
| 4,579,647 | 4/1986 | Smith | 208/111 |
| 4,714,592 | 12/1987 | Zanma et al. | 422/192 |
| 4,859,427 | 8/1989 | Konishi et al. | 422/159 |
| 4,937,051 | 6/1990 | Graven et al. | 422/194 |
| 5,157,054 | 10/1992 | Herbolzheimer et al. | 518/700 |
| 5,160,428 | 11/1992 | Kuri | 210/107 |
| 5,174,877 | 12/1992 | Cooper et al. | 204/193 |
| 5,362,453 | 11/1994 | Marsh | 422/197 |

FOREIGN PATENT DOCUMENTS

| | | | |
|---|---|---|---|
| 0450861A2 | 3/1991 | European Pat. Off. | C07L 1/04 |
| 0450860A2 | 3/1991 | European Pat. Off. | C07C 1/04 |
| 2193444 | 7/1987 | United Kingdom | B01J 12/100 |

OTHER PUBLICATIONS

Herbert Kolbel and Milos Ralek, The Fischer–Tropsch Synthesis in the Liquid Phase, Catal. Rev.–Sci. Eng., vol. 21(2), pp. 225–273 (1980).
G. Cut et al., Liquid–Phase Hydrogenation: The Role of Mass and Heat Transfer In Slurry Reactors, Studies in Surface Science and Catalysis, vol. 27, pp. 517–545 (1986) (L. Cerveny ed.).
G. v. d. Lee and V. Ponec, On Some Problems of Selectivity in Syngas Reactions on the Group VIII Metals, Catal. Rev.–Sci. Eng. vol. 29 (2&3), pp. 183–218 (1987).
M. A. Vannice, The Catalytic Synthesis of Hydrocarbons from Carbon Monoxide and Hydrogen, Catal. Rev.–Sci. Eng. vol. 14(2), pp.153–191 (1977).
Jan H. Fourie, The Sasol Slurry Bed Process to Convert Natural Gas to Middle Distillates, Urja Oil and Gas International, pp. 26–28 (1993).
Klaus Weissermel and Hans–Jurgen Arpe, Industrial Organic Chemistry, Important Raw Materials and Intermediates, pp. 88–89, 119–120, 181–182, 213–214, 219–220, 286–287, 301–302, 330–332 (1978).
Jiri Volf and Josef Pasek, "Hydrogenation of Nitriles," Catalytic Hydrogenation, Studies in Surface Science and Catalysis, vol. 27, (L. Cerveny ed.), pp. 105–115 (1986).

Primary Examiner—Werren B. Lone
Attorney, Agent, or Firm—Kirkpatrick & Lockhart

[57] ABSTRACT

A multi phase catalytic reactor in which a liquid product is separated from a slurry phase containing a finely divided solid catalyst in a liquid medium. The apparatus includes a vessel which contains a number of vertical reaction tubes, arranged to accommodate the slurry phase. Each tube has a filter member in contact with the slurry phase within the tube. The filter members thus define a filtrate zone which is separated from the slurry phase. Gaseous reactants are introduced into the slurry phase within the tubes and a heat exchange medium is circulated around the outside of the tubes.

36 Claims, 4 Drawing Sheets

SOLID/LIQUID SLURRY TREATMENT APPARATUS AND CATALYTIC MULTI-PHASE REACTOR

BACKGROUND TO THE INVENTION

The present invention relates to a reactor for conducting a continuous multi-phase catalytic reaction and is particularly, though not exclusively, applicable to the catalytic conversion of syngas, produced by the reforming of methane, to hydrocarbon fuels, by a Fischer-Tropsch type of synthesis. Other reaction systems for which the apparatus would be suitable include various slurry reactions for the production of petrochemicals, the production of oxygenates from synthesis gas and dehydrogenation reactions. Additionally, however, the apparatus is equally useful in solid/liquid slurry treatment applications.

DESCRIPTION OF PRIOR ART

Three-phase catalytic reaction systems are used in a number of chemical processes and their application in the petrochemical industry appears to be increasing. Among the three-phase systems in use, there are mechanically agitated slurry reactors, and loop and bubble column slurry reactors. These employ small catalyst particles dispersed in the liquid and so in most applications, the liquid will have to be separated from the slurry to remove liquid products or for catalyst regeneration purposes. In those cases where the liquid is an inert medium, occasionally, it may have to be replaced due to degradation or the build-up of impurities.

Mechanically agitated slurry reactors are particularly convenient for batch processes due to the low mass-transfer and heat resistance. These features also make them suitable for the determination of reaction kinetics in the laboratory. A serious disadvantage and limitation of this reactor type, however, is the difficulty in the separation of catalyst particles in any continuous operation.

Commercially, it is only mechanically agitated reactors that are used in the hydrogenation of double bonds of oils from cottonseed, soybean, corn, sunflower, etc. By employing a nickel catalyst, the products include margarine, shortening, soap and greases. The operation of bubble column slurry reactors is simple, since mechanically moving parts are avoided. Combined with the low diffusional resistance and efficient heat transfer, these reactors are attractive for many industrial processes. However, solid-liquid separation is usually performed outside the reactor in elaborate filtering and settling systems. The catalyst slurry is to be recycled to the reactor, sometimes with the use of a slurry pump. Thus, serious problems may be encountered in the continuous operation of bubble column slurry reactors.

As world oil resources diminish it is becoming more attractive to use natural gas as an energy source and methods of upgrading this to higher hydrocarbon fuels are increasing in importance.

It is therefore an object of the invention to provide a reactor which allows continuous method of conducting a multi-phase catalytic reaction which does not suffer the drawbacks of the prior art.

It is a particular object of the invention to provide such a reactor which is well suited to use in the conversion of natural gas via syngas to diesel fuel.

SUMMARY OF THE INVENTION

According to the present invention, there is provided a multi-phase catalytic reactor in which a liquid product is separated from a slurry phase containing a finely divided solid catalyst in a liquid medium, the apparatus comprising: a vessel; a plurality of vertical reaction tubes within the vessel, arranged to accommodate the slurry phase thereby defining a reaction zone; each tube having a filter member in contact with the slurry phase within the tube and defining a filtrate zone which is separated from the slurry phase; means for introducing gaseous reactants and/or other components into the slurry phase within the tubes; and means for circulating a heat exchange medium in the spaced defined by the internal walls of the vessel and the external walls of the tubes.

A recent report issued by the United States Department of Energy addressed the question of catalyst/wax separation in Fischer-Tropsch slurry reactor systems. The report concludes:

"Internal filters immersed in the reactor slurry, as used in some bench-scale or pilot-scale units, do not work successfully due to operational difficulties. A reactor with a section of its wall as a filter may be operable for a pilot plant but is not practicable for commercial reactors. Internal filters are subject to plugging risks, which may cause premature termination of the run, and commercial plants are not allowed to take chances."

The report states elsewhere that an internal filter within the reaction slurry has been employed in a research project. However, while a flow of filtrate was initially possible by employing a pressure differential, the filter soon became clogged and it was concluded that continuous operation would not be practical and that for a commercial-scale operation, it would be necessary to perform the solid/liquid separation outside the reactor.

The present Applicants have discovered that, contrary to this teaching, it is possible to provide a continuous reaction system for a Fischer-Tropsch synthesis in which it is not necessary to perform the solid/liquid separation in an external filter unit. Furthermore, a sufficiently high flow rate of filtrate for commercial operation can be achieved.

Preferably, therefore the reactor further includes means establishing a mean pressure differential across the filter members and means establishing fluid communication between a gas space above the filtrate zone and any gas space above the slurry phase in the tubes.

The apparatus may also be used for slightly different purposes, such as treatments of various kinds, e.g., ion exchange, purifications, removal of unwanted components (traces of impurities, discolourations).

It has been discovered by the present Applicants that the communication between the filtrate zone and the reaction or tretment zone can prevent the build-up of solid material on the filter element. [The term "reaction zone" will be used to refer to the reaction zone or the treatment zone, as appropriate.] This is believed to be achieved as follows. The turbulent motion of the slurry, as gas bubbles pass up through it, causes fluctuations or oscillations in pressure at the filter element. The fluid communication between the reaction zone and the filtrate zone facilitates or enhances these pressure fluctuations or oscillations.

Such a system is therefore relatively simple yet effective. The separation step, generally considered to be particularly problematic, can be achieved without undue complication and under proper operating conditions the filter member is self-cleaning.

The pressure differential may result from the hydrostatic pressure arising from the slurry in the reaction vessel having a higher hydrostatic level than the filtrate in the filtrate zone.

The communication between the space above the slurry in the reaction zone and the space above the filtrate in the filtrate zone prevents the build up of pressure differentials in excess of that corresponding to the hydrostatic pressure.

Preferably, the amplitude or magnitude of the fluctuations or oscillations in the pressure differential across the filter element is about the same magnitude or greater than the mean value of the static pressure differential. Preferably the mean pressure differential across the filter element should be kept at a rather low level, typically less than 6 mBar (600Pa). If the mean pressure differential is below a critical vale (6 mbar in case of the exemplified system), the filter is self cleaning. With slightly higher values, build-up of a cake of particles on the filter surface will occur, as one would expect for a filter, and the capacity will gradually decrease. This cake will disappear if the flow through the system is reversed (backflushed), and the original capacity will be regained. With even higher values, the catalyst particles may penetrate into the filter. If this happens, the decreased capacity may be permanent, and increased capacity by backflushing the filter may not be possible.

Preferably, the filter element comprises a fine meshed screen, helically wound threads, fine vertical threads or sintered metal particles. Preferably, the surface of the filter element which is in contact with the slurry is rendered smooth. The filter element may be provided by a portion of the wall of the respective tube which is composed of a filter material.

The filter element material and catalyst are preferably selected so that the maximum hole or pore size in the filter element is of the same order of magnitude as the catalyst particle size. The particle size is preferably not less than half the pore size.

The means for introducing gaseous reactants or components may comprise any suitable means for providing the reactants as a stream of bubbles, such as a bubble cap plate, a plurality of nozzles, a frit plate, etc, preferably located at the bottom of each tube. The reactants may be CO and $H_2$, for example from the reforming of natural gases, and the products may be methanol and higher hydrocarbons.

The pressure fluctuation value may be of the order of the pressure differential, for example from 10 to 200% of the pressure differential. The actual value of the pressure differential may be from 1 to 100 mBar, preferably 2 to 50 mBar.

Preferably, there is an outlet from each filtrate zone arranged to provide a constant level for the filtrate in the filtrate zone. In one embodiment, the outlet from the filtrate zone comprises an inverted U-shaped pipe whose top section defines the liquid level in the filtrate zone. In an alternative embodiment, the outlet from the filtrate zone includes a weir within the filtration section which defines the liquid level in the filtrate zone. In a further embodiment, the outlet from the filtrate zone comprises an upwardly extending pipe within the filtrate zone which is open at a level which defines the liquid level in the filtrate zone.

In another embodiment, a level indicator senses the level of the filtrate in the filtrate zone and controls the operation of a valve in a filtrate outlet from the filtrate zone in order to achieve a desired filtrate level in the filtrate zone.

Preferably, the reactor is provided with a gas outlet from any filtrate zone. Preferably, each tube has an inlet/outlet through which slurry can be introduced or discharged. Preferably, the means for circulating a heat exchange medium comprise a fluid inlet to and a fluid outlet from the portion of the vessel in which the tubes extend.

In a preferred embodiment, there is a generally horizontal tube collector plate supporting the tubes within the vessel and separating the vessel into an upper portion and a lower portion, each tube having a filter member in contact with the slurry phase within the tube and positioned in the upper portion of the vessel thereby defining a filtrate zone outside the tubes in the upper portion of the vessel.

Preferably, the tubes have openings above the filtrate zone, and the ends of the tubes may be open. The tubes may each include an increased diameter portion above the level of its respective filter member. Preferably, the tubes are open to a common gas space above the filtrate zone thereby providing the said fluid communication between the gas space above the filtrate zone and the gas spaces above the slurry phase in the tubes. Preferably, the upper portion of the vessel includes a dome over the top of the filtrate zone to define the common gas space.

Preferably, each tube has a sleeve surrounding its filter member in the filtrate zone. Preferably, each sleeve extends upwards to a level somewhat above the level of the filtrate in the filtrate zone.

In another embodiment, each filter member is located at the upper portion of its respective tube within a housing which surrounds the upper portion of the tube and thereby defines the filtrate zone. Alternatively, each filter member may be located within the upper portion of its respective tube and defines internally the filtrate zone. In either case, the various reaction zones may have respective gas outlets connected to a common main. Preferably, also, each filtrate zone has an outlet which is connected to a liquid product collector main.

The tubes may have external fins to increase the area of heat transfer to the heat exchange medium. Possibly, the portion of the vessel in which the heat exchange medium is circulated is divided vertically into two or more sections, each section having its own heat exchange medium inlet and outlet.

An increased production rate may be achieved by providing a higher effective filter area. This may be achieved by adopting a more intricate or complex filter element profile.

The invention is particularly well adapted for use in a method of converting natural gas (methane) to higher hydrocarbon fuels which involves initially converting the natural gas into synthesis gas, either by steam reforming, partial oxidation, a combination of the two, or otherwise reforming the methane to produce carbon monoxide and hydrogen, subjecting the CO and $H_2$ to catalytic conversion by a Fischer-Tropsch synthesis to form higher hydrocarbon fuels such as liquid paraffin waxes, and subsequently separating and/or cracking these products to produce the required range of hydrocarbons.

When diesel fuel is produced in this way it is vastly superior to conventional diesel in terms of its quality and properties. Firstly, it contains no sulphur, which is important from an environmental point of view. Secondly, it has a very high cetane number and can therefore be blended with lower grades of diesel fractions in order to produce a product which meets premium range standards. Thirdly, it contains virtually no harmful compounds that generate soot when burned and needs fewer additives for problem free use at low temperatures.

Preferably, the heat exchange medium is a liquid at its boiling point. Conveniently, the medium is water, whereby the heat generated by the reaction is used to generate steam. Thus, substantially all the heat of reaction can be used to generate medium temperature/medium pressure steam, and this can be used as a valuable energy source.

DESCRIPTION OF THE DRAWINGS

The invention may be carried into practice in various ways and some embodiments will now be described by way of example with reference to the accompanying drawings, in which.

DESCRIPTION OF THE PREFERRED EMBODIMENTS

Figure 1:
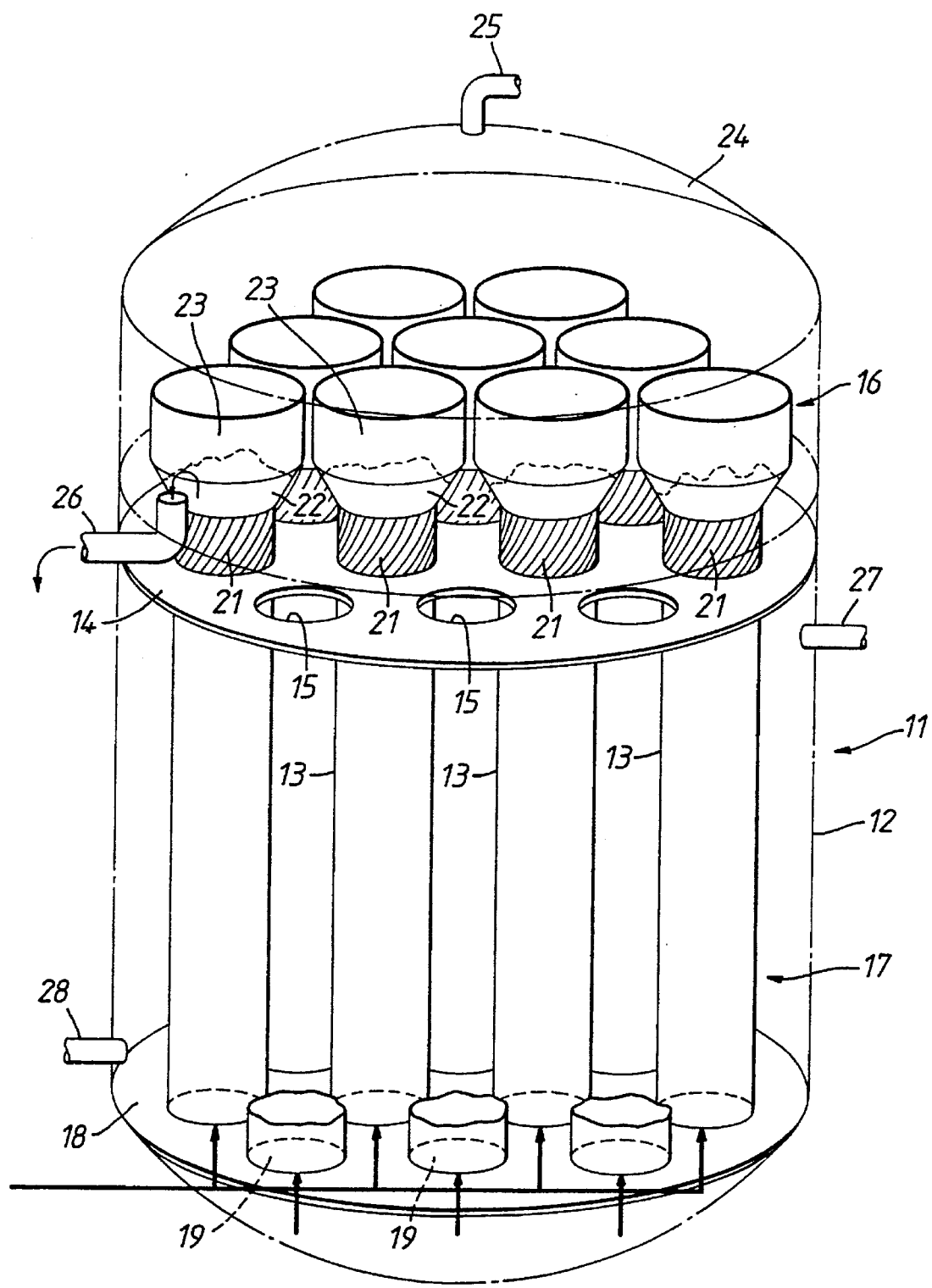
FIG. 1 is a schematic perspective view of a three-phase slurry reactor in accordance with the invention.

As shown in FIG. 1, the reaction apparatus 11 includes a reactor vessel 12 containing a series of reactor tubes 13.

A main collector plate 14 supports the tubes 13 by means of openings 15 through which the tubes 13 pass and divides the vessel internally into an upper portion 16 and a lower portion 17. At the bottom of the lower portion 17, a lower collector plate 18 supports the tubes 13 and at the bottom of each tube 13 there is a gas distributor 19.

Above the main collector plate, a portion of the wall of each tube 13 is constituted by a filter element 21. In the illustrate embodiment, the filter element is a sinter material. Above the filter element 21, each tube 13 has a part-conical section 22 leading to a top section 23 of increased diameter (though other means may be provided for breaking-up foam or preventing foam carry-over). The top section 23 of each tube 13 is open. The upper portion 16 of the vessel 11 is closed by a dome 24 which has a gas outlet 25. The upper portion 16 also has a liquid outlet 26.

Figure 2:
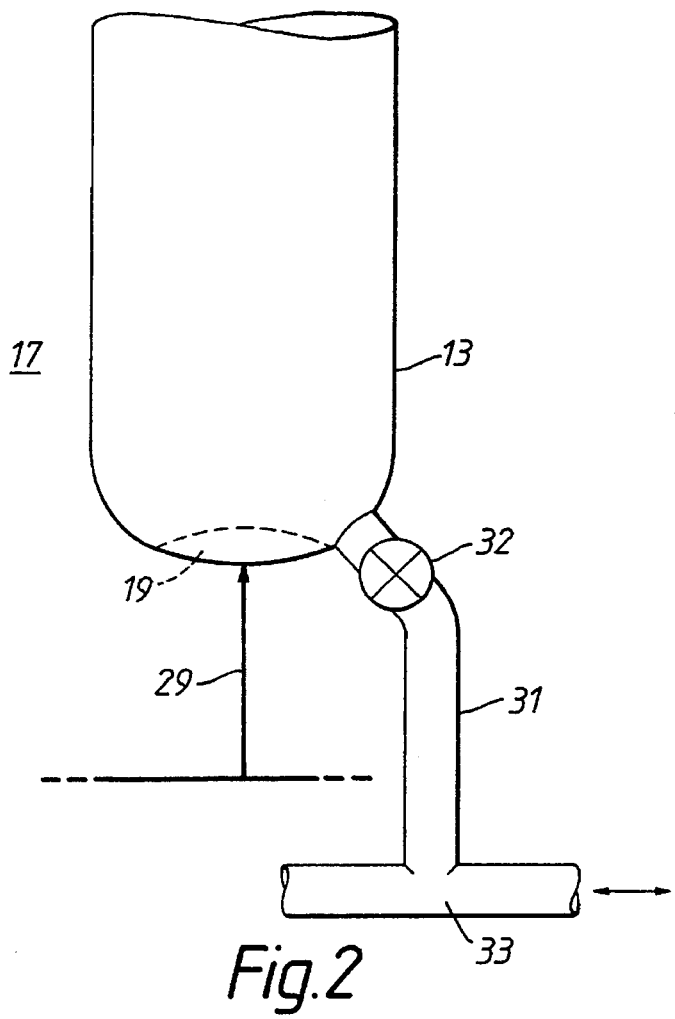
FIG. 2 is a simplified sketch of the lower part of a reaction tube.

The lower portion 17 of the vessel 11 has an inlet 27 and an outlet 28 for a heat exchange medium, such as water. As shown in FIG. 2, a gaseous reactant inlet 29 leads to the gas distributor 19 at the bottom of each tube 13. In addition, there is a slurry inlet/outlet 31 at the bottom of each tube 13, controlled by a valve 32, and leading to a common handling pipe 33. The piping system 31,32,33 is preferably located beneath the collector plate 18, as shown.

Figure 3:
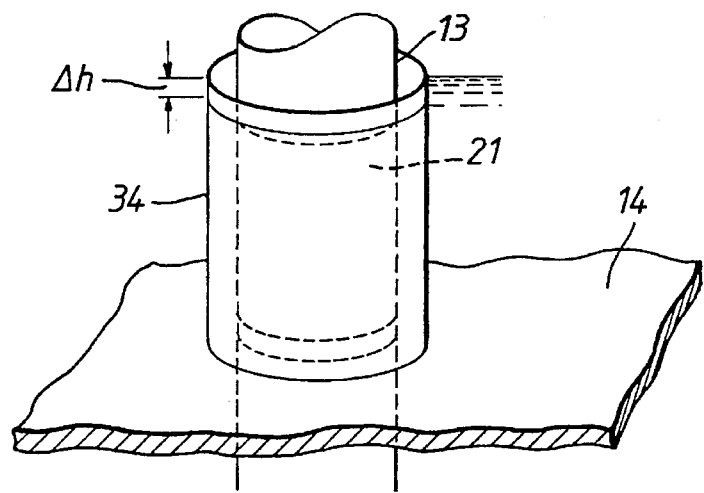
FIG. 3 is an isometric sketch of the upper part of a reaction tube.

As shown in FIG. 3, the filter element 21 at the top of each tube 13 is surrounded by the sleeve 34. The sleeve 34 is spaced from the filter element 21 and extends upwards from the main collector plate 14 to a level slightly above the top of the filter element 21.

In use, in a Fischer-Tropsch synthesis, the tubes 13 are charged with a slurry of a finely divided FT catalyst in a liquid medium comprising the desired products of the reaction. The tubes thus define a reaction zone. The slurry is filtered by the filter elements 21 and the filtrate is retained above the main collector plate 14 in the upper portion 16 of the vessel. The upper portion 16 thus defines a filtrate zone. Gaseous reactants are introduced into the tubes via the distributors 19 and pass through the slurry as gas bubbles.

Gaseous products are recovered via the outlet 25. Liquid filtrate is recovered via the outlet 26. The outlet 26 is in the form of an upturned pipe within the filtrate zone and thus services as a constant level device for the filtrate. It maintains the filtrate in the filtrate zone at a level blow the slurry level in the tubes 13 and thus establishes a pressure gradient across the filter elements 21. The enlarged portion 22, 23 of each tube helps to prevent foaming at the top as gases escape the slurry.

The temperature of the reaction within the tubes 13 is controlled by the heat exchange medium which circulates in the lower portion 17 of the vessel.

If the slurry in a tube 13 is to be regenerated, the valve 32 is opened and the contents of the tube 13 will discharge through the slurry inlet/outlet 31 into the handling pipe 33. Used catalyst may be regenerated in a separate regeneration plant and the tube 13 reloaded with new or regenerated slurry via the same (or separate) inlet/outlet 31 and handling pipe 33. Since the reactor will include a large number of reactor tubes 13, discharge and reloading of one of the reactor pipes at any time will have little or no practical effect on the operation of the total reactor system.

When one of the reactor tubes 13 is emptied, the filtrate product above the plate 14 will tend to flow back through the filter element 21 of the emptied tube 13. Consequently, the filtrate level would begin to drop, which would be undesirable. This disadvantage is overcome by the cylindrical sleeve 34 surrounding the upper portion of the tube 13 in the filtrate zone. The presence of the sleeve 34 prevents the level of the filtrate outside the sleeve 34 dropping when the tube 13 is emptied (FIG. 3). The height of the sleeve 34 is adjusted to the filtrate level in the filtrate zone which is defined by the vertical position of the end of the outlet 26, so as to achieve a small step $\Delta h$ between the height of the sleeve 34 and the filtrate level.

Figure 4:
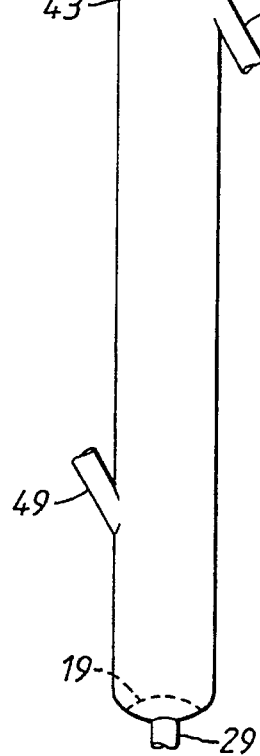
FIG. 4 is a schematic vertical section through a second embodiment.

FIG. 4 shows an alternative form of reactor, in this case each tube 43 has a similar filter element 21 forming part of its wall in the upper part. However, the filtrate zone is defined by an outer housing 44 which surrounds the upper part of the tube 43, including the filter element 21. The filtrate level is determined by the position of an outlet 45 from the housing 44. The level of the slurry in the tube 43 is again above that of the of the filtrate in order to provide a pressure differential. Fluid communication between the gas space above the filtrate and the gas space above the slurry may be provided.

The filtrate outlet 45 is shown joining a common filtrate handling pipe 46. Similarly, a gas outlet 42 from the top of the tube 43 joins a common gas main 47. The tube 43 is also shown having an inlet 48 and an outlet 49 for the slurry. These may also be connected to a common inlet and outlet respectively (not shown).

Figure 5:
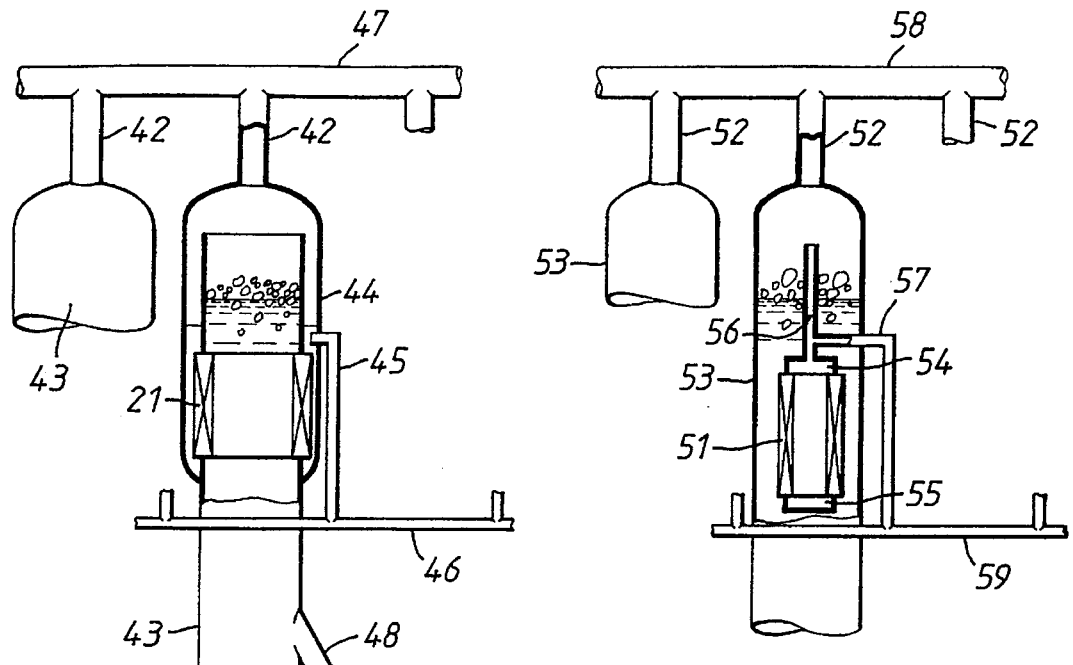
FIG. 5 is a partial vertical cross-section of a further embodiment.

The embodiment shown in FIG. 5 differs from that shown in FIG. 4 in that a cylindrical filter element 51 is located within the slurry in the upper part of the tube 53. The filter element 51 has a cap 54 and a base 55. Together, the filter element 51 and the cap 54 and base 55 define internally the filtrate zone. A pipe 56 extends from the cap into the space above the slurry. A liquid filtrate outlet 57 extends from the pipe 56 and thus defines the filtrate level in the filtrate zone. Again, the filtrate level is below the level of the slurry in the tube 53. The tube 53 has a gaseous products outlet 52 which joins a common gas main 58. The filtrate outlet 57 joins a common filtrate handling pipe 59.

In both the embodiments shown in FIGS. 4 and 5, the tubes 43,53 are submerged in the cooling medium within the vessel. The submersion may be total or partial, to the extent required to achieve the desired temperature control.

Figure 6:
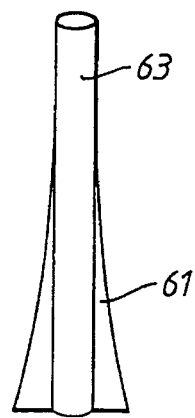
FIG. 6 and 7 is a schematic of a temperature gradient along the reactor tube.
Figure 7:
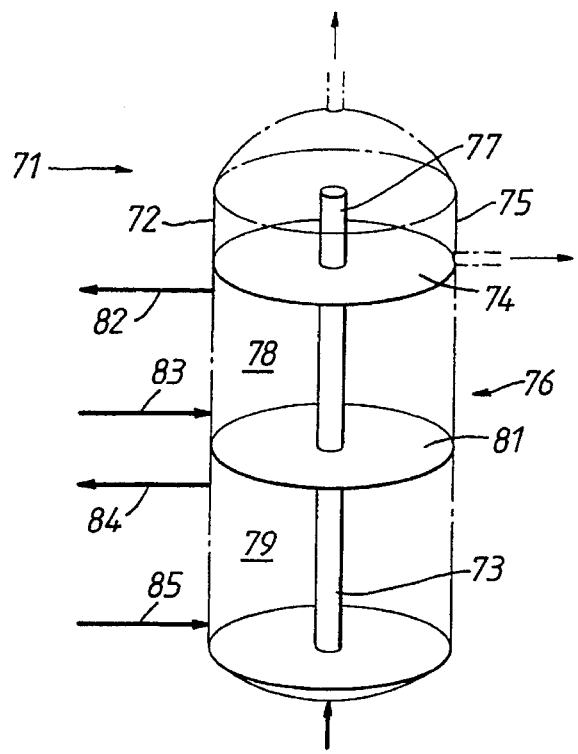

In all the embodiments described above, there may in practice be a temperature gradient along the length of the reactor tubes 13,43,53. This can be compensated for in various ways, two of which are shown in FIGS. 6 and 7. In FIG. 6, fins 61 are provided in the outside surface of the tubes 63. This will increase the heat exchange area in the bottom of the reactor where heat generation is highest.

In FIG. 7, the reactor 71 shown is generally similar to that shown in FIG. 1, with only one reactor tube 73 shown (for reasons of clarity) within the vessel 72. A collector plate 74 divides the vessel into an upper section 75 which constitutes the filtrate zone and a lower section 76 which constitutes the cooling zone. The tubes 73 have a filter element 77 above the collector plate 74 in the filtrate zone. However, the cooling zone is divided into two sections 78,79 by a second collector plate 81. Each of the sections 78,79 has a respective cooling medium inlet 82,84 and a cooling medium outlet 83,85. The cooling rate in the lower section 79 would be greater than that in the higher section 78. This could be achieved for example by employing a lower cooling medium inlet temperature for the lower inlet 85 shown for the higher inlet 83.

Another way to avoid a temperature gradient might be to employ a less active catalyst or milder reaction conditions. This would increase the reactor size but may still be economically preferable.

Figure 8:
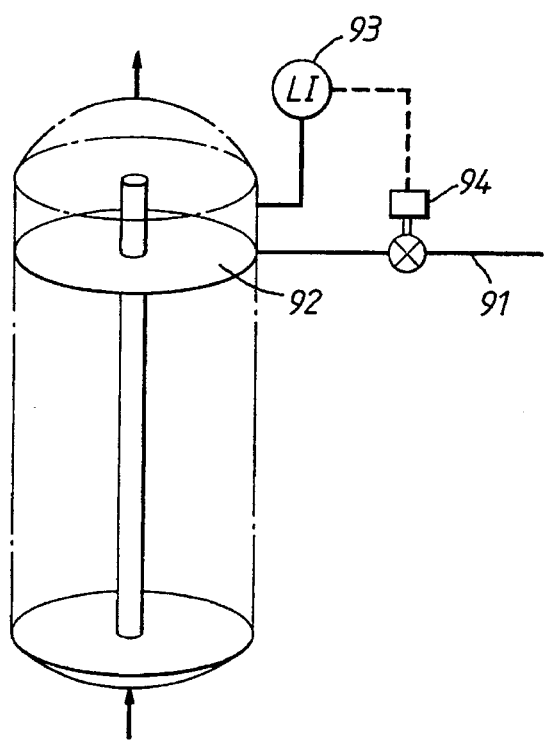
FIG. 8 is a schematic of another embodiment in which the filtrate is adjustable.

FIG. 8 shows another embodiment in which the filtrate level is adjustable. In this case the filtrate outlet 91 is at the bottom of the filtrate zone, effectively at the collector plate 92. The filtrate zone is measured by a level indicator 93. The filtrate amount withdrawn from the bottom of the filtrate zone is controlled by a regulating valve 94 in the outlet 91. The position of the valve 94 is regulated by a signal from the level indicator 93 or by an operator Using this system, the level in the filtrate zone can be adjusted. In a system with product withdraw from the top of the filtrate zone, the level may not be adjustable.

The invention will now be further illustrated in the following Example which is a simulation of a system in accordance with the invention.

EXAMPLE

A slurry bubble column Fischer-Tropsch reactor is simulated using a two phase quasi homogenous one dimensional model. Typical performance data for a catalyst described in U.S. Pat. No. 4,801,573 is used as input for the simulation. The process parameters were:

Pressure: 20 bar ($2 \times 10^6$Pa)

Temperature: 220° C.

$H_2$:CO ratio: 2:1

Superficial gas velocity: 10cm/s

Catalyst Loading: 15 wt %

With these typical process conditions, for a medium conversion process, using a reactor with 2000.30 m I.D. tubes, it is necessary to have tubes 7 m long to get 70% conversion. With a pure synthesis gas as feed, the resulting mass balance (kg/h) is: (Numbers for each tube are given in parenthesis.)

|  | Gas in | Gas out | Liquid out | Total product |
| --- | --- | --- | --- | --- |
| $H_2$ | 3.322 (17) | 1.003 (5) | 1 (–) | 1.004 (5) |
| CO | 23.065 (115) | 7.344 (37) | 5 (–) | 7.349 (37) |
| $H_2O$ | — | 9.942 (50) | 70 (–) | 10.012 (50) |
| $CO_2$ | — | .117 (1) | — | 117 (1) |

-continued

|  | Gas in | Gas out | Liquid out | Total product |
| --- | --- | --- | --- | --- |
| $C_1$ | — | .364 (2) | 1 (–) | 365 (2) |
| $C_2$-$C_4$ | — | .587 (3) | 2 (–) | 589 (3) |
| $C_{5+}$ | — | 3.215 (15) | 3.736 (19) | 6.951 (34) |
| Σ | 26.387 (132) | 22.572 (113) | 3.815 (19) | 26.387 (132) |

The heat generated by the reaction in the process is calculated to be approximately 23.700 kW (118.5 kW for each tube). A negligible amount of heat is assumed to be removed by the products steams, meaning that all heat must be removed through the tube walls. The heat is removed by the evaporation of water on the outside of the tubes. With the given set of process conditions, and a delta T of approximately 25K across the tube wall, approximately 43.1 ton medium pressure steam per hour will be granted.

Suitable ranges for the process parameters might be:
Pressure: 10–50 bar (1 to 5 MPa) Temperature: 200°–300° C.

H2:CO ratio: 0.5:13:1

Superficial gas velocity: 5–50cm/s

Catalyst loading: 5–50 wt %

Naturally, an optimal tube diameter can be determined. This optimal tube diameter is the diameter which gives exactly the necessary heat exchange surface. The diameter can be expressed in the following terms: Given a certain production, m (kg/h), and a volumetric production ratio, r (kg/m³h) defined by catalyst behaviour and process conditions, the total reactor volume, V (m³) is defined. The reactor volume is given by the total cross section area and the tube length: $V = n \times \pi \times r^2 \times h$, where n is the number of tubes, r is the tube diameter and h is the tube length. Assuming the production ratio is independent of the tube diameter, several combinations of the tube diameter and the number of tubes are possible. The necessary heat exchanger surface is defined by the equation $Q = U \times A \times \Delta T$, where $A = 2 \times \pi \times r_i \times n$. The optimal tube diameter is that which fulfils both the above equations.

Numerous characteristics and advantages of the invention have been set forth in the foregoing description. It will be understood, of course, that this disclosure is, in many respects, only illustrative. Changes can be made in details, particularly in matters of shape, size and arrangement of parts without exceeding the scope of the invention.

We claim:

1. A multi-phase catalytic reactor in which a liquid product is separated from a slurry phase which contains a finely divided solid catalyst in a liquid medium, the apparatus comprising: a) a vessel; b) a plurality of vertical reaction tubes within said vessel, said tubes being arranged to accommodate said slurry phase and thereby defining a reaction zone; each tube having a filter member in contact with said slurry phase within said tube, said filter members collectively defining a filtrate zone which is separated from said slurry phase; c) means for introducing gaseous reactants and/or other components into said slurry phase within said tubes; and d) means for circulating a heat exchange medium within a portion of said vessel defined by internal walls of said vessel and external walls of said tubes.

2. A reactor according to claim 1, further including means establishing a mean pressure differential across said filter members.

3. A reactor according to claim 2, said filtrate zone having a first gas space thereabove, said slurry phase having a second gas space thereabove, said reactor further including means establishing fluid communication between said first and second gas spaces.

4. A react according to claim 1, wherein said means for introducing said gaseous reactants is arranged to introduce said gaseous reactants as a stream of bubbles into said slurry phase.

5. A reactor according to claims 2, wherein said mean pressure differential across each said filter member is achieved by means of a difference in level between said slurry in said reaction zone and said filtrate.

6. A reactor according to claim 1, further including an outlet from said filtrate zone arranged to provide a constant liquid level for said filtrate in said filtrate zone.

7. A reactor according to claim 6, wherein said outlet from said filtrate zone comprises a pipe section having a portion which defines an inverted U-shape, the top part of said inverted U-shape defining said liquid level in said filtrate zone.

8. A reactor according to claim 6, wherein said outlet from said filtrate zone includes a weir which defines said liquid level in said filtrate zone.

9. A reactor according to claim 6, wherein said outlet from said filtrate zone comprises an upwardly extending pipe within said filtrate zone, said upwardly extending pipe being open at a level which defines said liquid level in said filtrate zone.

10. A reactor according to claim 1, further including a level indicator which senses the level of said filtrate in said filtrate zone an outlet from said filtrate zone and a valve in said outlet from said filtrate zone, said indicator being arranged to control the operation of said valve in order to achieve a desired filtrate level in said filtrate zone.

11. A reactor according to claim 1, further including a gas outlet from said filtrate zone.

12. A reactor according to claim 1, wherein each said tube has an inlet/outlet through which slurry can be introduced and discharged.

13. A reactor according to claim 1, wherein said means for circulating said heat exchange medium comprises a fluid inlet to and a fluid outlet from a portion of said vessel in which said tubes extend.

14. A reactor according to claim 1, wherein each said filter member includes a filter material selected from the group consisting of a fine meshed screen, helically wound metal threads, sintered particles of metal and sintered particles of a ceramic material.

15. A reactor according to claim 14, wherein said filter material has a surface which is in contact with said slurry and said surface is rendered smooth.

16. A reactor according to claim 1, wherein each said filter member is provided by a portion of the wall of the respective tube being composed of a filter material.

17. A reactor according to claim 1, further including a generally horizontal tube collector plate supporting said tubes within said vessel and separating said vessel into an upper portion and a lower portion, each said tube having a filter member in contact with said slurry phase within said tube and positioned in an upper portion of said vessel thereby defining said filtrate zone outside said tubes in said upper portion of said vessel.

18. A reactor according to claim 1, wherein said tubes have respective openings above said filtrate zone.

19. A reactor according to claim 18, wherein the top ends of said tubes are open.

20. A reactor according to claim 19, wherein said tubes each include an increased diameter portion above the level of the respective filter member thereof.

21. A reactor according to claim 3, wherein a common gas space is defined above said filtrate zone and said tubes are open to said common gas space thereby providing fluid communication between said common gas space above said filtrate zone and any gas above said slurry phase in said tubes.

22. A reactor according to claim 21, wherein said vessel includes at the upper portion thereof a dome over said filtrate zone thereby defining said common gas space.

23. A reactor according to claim 1, wherein each said tube includes a sleeve surrounding the respective filter member thereof in said filtrate zone.

24. A reactor according to claim 23, wherein each said sleeve extends upwards to a level somewhat above the level of said filtrate in the filtrate zone.

25. A reactor according to claim 1, further comprising a housing which surrounds an upper portion of each said tube and each said filter member is located at an upper portion of respective tube thereof within said housing thereby defining said filtrate zone.

26. A reactor according to claim 1, where each said filter member is located within an upper portion of the respective tube thereof and defines said filtrate zone internally.

27. A reactor according to claim 25, further comprising a gaseous product collector pipe and a gas outlet from said reaction zone, said gas outlet being connected to said collector pipe.

28. A reactor according to claim 25, further comprising a liquid product collector main and a gas outlet from each filtrate zone, each said outlet being connected to said collector main.

29. A reactor according to claim 26, further comprising a gaseous product collector pipe and a gas outlet from said reaction zone, said gas outlet being connected to said collector pipe.

30. A reactor according to claim 26, further comprising a liquid product collector main and a gas outlet from each filtrate zone, each said outlet being connected to said collector main.

31. A reactor according to claim 1, wherein external fins are fitted to said tubes to increase the area of heat transfer to said heat exchange medium.

32. A reactor according to claim 1, wherein said portion of said vessel in which said heat exchange medium is circulated is divided vertically into at least two sections, each said section having a respective heat exchange medium inlet and heat exchange medium outlet.

33. The use of a reactor according to claim 1 to conduct a Fischer-Tropsch synthesis reaction.

34. The use of a reactor according to claim 33, wherein hydrogen and carbon monoxide are supplied to said tubes, said tubes containing a slurry of liquid hydrocarbons and a finely divided Fischer-Tropsch catalyst.

35. The use of a reactor according to claim 34, wherein said heat exchange medium is a liquid at its boiling point.

36. The use of a reactor according to claim 35, wherein said medium is water, whereby heat generated by the reaction is used to generate steam.

* * * * *